United States Patent [19]
Tanaka et al.

[11] Patent Number: 5,480,654
[45] Date of Patent: Jan. 2, 1996

[54] PROLONGED RELEASE DOSAGE FORM OF DRUG AND METHOD FOR PRODUCING THE SAME

[75] Inventors: Nagahiko Tanaka; Narimichi Takei; Kazuomi Unosawa, all of Tokyo, Japan

[73] Assignee: Freund Industrial Co., Ltd., Tokyo, Japan

[21] Appl. No.: 333,248

[22] Filed: Nov. 2, 1994

Related U.S. Application Data

[63] Continuation of Ser. No. 780,941, Oct. 23, 1991, abandoned.

[30] Foreign Application Priority Data

Oct. 23, 1990 [JP] Japan ..................... 2-285539

[51] Int. Cl.⁶ ............. A61K 9/14; A61K 9/16; A61K 9/22
[52] U.S. Cl. ............. 424/490; 424/494; 424/495; 424/497; 424/498; 424/468; 427/2.14; 427/2.21; 427/212; 427/421
[58] Field of Search ............. 424/474, 494–495, 424/498–499, 470; 427/3, 212, 421, 2.14, 2.21

[56] References Cited

U.S. PATENT DOCUMENTS

| | | | |
|---|---|---|---|
| 4,592,302 | 6/1986 | Motoyama et al. | 118/303 |
| 4,702,919 | 10/1987 | Kitamori et al. | 424/480 |
| 4,764,378 | 8/1988 | Keith et al. | 424/435 |
| 4,983,401 | 1/1991 | Eichel et al. | 424/494 |

FOREIGN PATENT DOCUMENTS

| | | |
|---|---|---|
| 8402843 | 8/1984 | Egypt . |
| 212751 | 3/1987 | European Pat. Off. . |
| 251680 | 1/1988 | European Pat. Off. . |
| 257310 | 3/1988 | European Pat. Off. . |
| 1511852 | 5/1978 | United Kingdom . |
| 2186485 | 8/1987 | United Kingdom . |

*Primary Examiner*—Edward J. Webman
*Attorney, Agent, or Firm*—Kane, Dalsimer, Sullivan, Kurucz, Levy, Eisele and Richard

[57] ABSTRACT

A prolonged release dosage form of drug made by coating a surface of an ungranulated medicinal particle with a water-insoluble material which is physiologically acceptable and does not dissolve in water and gastric juice; and then, granulating or tableting the coated medicinal particles.

5 Claims, 3 Drawing Sheets

1

PROLONGED RELEASE DOSAGE FORM OF DRUG AND METHOD FOR PRODUCING THE SAME

This application is a continuation of application Ser. No. 07/780,941, filed Oct. 23, 1991, now abandoned.

BACKGROUND OF THE INVENTION

1. Field of the Invention

The present invention relates to a prolonged release dosage form of a drug and a method for producing the same.

2. Related Art Statement

A prolonged release dosage form of a drug is a dosage form designed so that a medicinal agent is released or dissolved gradually within a body. There are many kinds of methods for controlling the dissolution of a medicinal agent by prolonged release. Among them, the usual method is one wherein a coating layer is provided on the surface of a granule or a tablet containing a medicinal agent to control the release of the medicinal agent, or one wherein a medicinal agent is dispersed in wax or a water insoluble matrix to control its release.

In the prolonged release dosage forms in which the release of a medicinal agent is controlled by the coating layer, a medicinal agent is first formed in granules or tablets together with an excipient, and then, a coating layer is formed on the surface thereof. This is based on the concept that when a coating layer is formed under constant conditions on a particle having uniform size and shape, the coating layer displays a uniform properties. Therefore, by processing the drug to be coated into a granule or tablet, whose size and shape are easily controllable, the rate of release of the medicinal agent can be decreased.

In addition, when a coating layer is provided on the surface of a granule or a tablet containing a medicinal agent, it is desired that the particle size thereof is as small as possible. The reason for this is that when there is a defect in the coating layer on the surface of the granule or the tablet, or there is a variation in the properties of the coating layer among the granules or tablets, the more the number of granules or tablets to be dosed at one time, the smaller the influence caused by the defect or in the dosage for one time. Thus, the smaller the particle size of the granules or tablets, the higher the safety of the dosage form.

Moreover, the release of the medicinal agent from the granule or the tablet is related not only to physical processes in the coating layer, such as the diffusion of water and the medicinal agent through the coating layer, the dissolution of the coating layer itself and the like, but also to complicated physical processes within the granule or the tablet, such as the diffusion of water, the dissolution of the medicinal agent, the mixing of water with the dissolved medicinal agent, the diffusion of the solution of the medicinal agent and the like. Particularly, the larger the particle size of the granule or tablet, the larger the contribution of the latter processes to the release of the medicinal agent. Therefore, it is advantageous to provide a coating layer on the surface of a granule or a tablet having a small particle size in view of simplicity in analysis, and ease in designing dosage form and obtaining one showing a desired dissolution curve.

However, a special technique has been required in order to process a granule or tablet containing a medicinal agent to less than or equal to 100 μm. particle size i.e. such as the technique using a ball mill, a colloid mill, a jet mill or the like. Further, it has been impossible to form a coating layer on the surface of such a small particle. As a result, particles having a diameter of more than 200 μm, or at the smallest, more than 100 μm. can be used under conventional technical conditions.

The present inventors developed a granulating-coating apparatus capable of providing a good coating layer on the surface of a small particle having a particle size of less than or equal to 100 μm. Further, they showed that a dosage form obtained by coating material powder, i.e. particles before granulation, of a medicinal agent such as theophylline with a layer of wax using the above apparatus has a prolonged release effect (Abstracts of Oral presentations in Autumn Session of Society of Powder Technology, p.77, 1989; Japanese Patent Application Laid-open Nos. 1-176921 and 1-273337). However, no preferable prolonged release dosage form was obtained when only the above granulating-coating apparatus was used, since the prolonged release effect was not sufficient and its dissolution curve was a first-order dissolution curve.

SUMMARY OF THE INVENTION

An object of the invention is to provide a prolonged release dosage form having excellent prolonged release effect.

According to the present invention, a dosage form is prepared by forming a coating layer on powder of a medicinal agent using the above granulating-coating apparatus, and then, tableting it together with an excipient. The present inventors have found that the dissolution curve of the present dosage form is unexpectedly different from that of the coated powder before tableted and from that of a conventional dosage form in which the powder is simply mixed with an excipient and tableted, the dissolution curve of the dosage form of the present invention being a preferable one.

Moreover, the inventors have found that by adding a water-soluble polymer material when the powder of the medicinal agent coated with the above granulating-coating apparatus is tableted, the dissolution curve obtained becomes more preferable.

The prolonged release dosage form according to the invention is prepared by forming a coating layer of a water-insoluble material on the surface of medicinal particles before granulation, then mixing them with an excipient followed by granulation to obtain a dosage form.

As the medicinal particle, any medicinal material the form of powder or particle may be used. Examples are theophylline, nifedipine, nicardipine hydrochloride, propanolol hydrochloride, pindolol, isosorbide nitrate and the like.

It is preferable that the medicinal particles before granulation have particle sizes within the range of from 0.1 to 100 μm. Although a coating layer can be formed on the surface of medicinal agent having a diameter of less than 0.1 μm, the quantity ratio of the coating layer to the medicinal agent becomes too large in this case, so that it is not practical. On the other hand, when the particle size of the main medicinal agent is larger than 100 μm, its prolonged release effect becomes inferior.

The water-insoluble material for forming the coating layer may be any physiologically acceptable material provided that it does not dissolve in water and gastric juice. Examples of the water-insoluble material are (1)hydrophobic materials, such as oil, wax, higher alcohol, higher fatty acid and the like; (2)water-insoluble polymer materials, such as ethylcellulose, shellack and the like; and (3)polymer materials for enteric coating, such as hydroxypropyl methylcellulose phthalate, methacryl acid-methacryl acid ester copolymer, carboxymethylethyl cellulose and the like.

No particular restriction is imposed on the method for coating ungranulated medicinal particles with the above water-insoluble materials, but it is preferred that the granulating-coating apparatus developed previously by the inventors (see the aforementioned literature) is used. The present invention can be performed by using the above apparatus.

As a reference, FIG. 3 shows the outline of the above granulating-coating apparatus. This granulating-coating apparatus has, in the bottom of a processing cylinder 1, a nozzle 2a for powder material for supplying ungranulated medicinal particles and a nozzle 2b for liquid material for supplying a water-insoluble material. The medicinal particles are supplied through a feeder 3, and jetted from the nozzle 2a into the processing cylinder 1 by the pressure of air supplied from a compressed-air source 4a. On the other hand, a solution, a disperse liquid, or a melt of a water-insoluble material stored in a container 5 is sucked by a pump 6, and jetted from the nozzle 2b into the processing cylinder 1 by the pressure of air supplied from a compressed-air source 4b.

The medicinal particles and the solution of the water-insoluble material, both jetted into the processing cylinder 1, collide with each other in the processing cylinder 1, and the solution of the water-insoluble material adheres on the surface of the medicinal particles. On the side wall of the processing cylinder 1, air inlets 7 are provided for supplying drying air. The drying air is usually cooled air or air heated by a heater 8 to a predetermined temperature, and the amount thereof flowing into the processing cylinder 1 is controlled by a flow-rate controlling means 9 provided in the path to each air inlet 7. The solvent of the water-insoluble material solution adhered on the surface of the main medicinal particles evaporates by the drying air supplied from the above air inlets 7 into the processing cylinder 1, thereby to form a coating layer. In the upper part of the processing cylinder 1, a collecting path 10 is provided. The coated main medicinal particles obtained are exhausted out of the processing cylinder 1 by the sucking force of a blower 11, descend in a cyclone 12, and are collected in a collecting vessel 13 placed under the cyclone 12.

In order to make a dosage form by granulating the thus-obtained coated main medicinal particles, a known granulating technique can be applied. That is, after mixing the coated medicinal particles described above with an excipient, a binder, a disintegrator, a lubricant and the like, they are granulated by a known method such as tableting, tumbling granulation, stirring granulation, fluidizing granulation or the like, and, if necessary, are further coated with a sugar or other coating, thus obtaining a dosage form.

By adding a water-soluble polymer material when the above coated medicinal particles are granulated, the prolonged release effect of the dosage form of the invention is further improved. Examples of the water-soluble polymer material are (1)cellulose ethers, such as hydroxyethyl cellulose, hydroxypropyl cellulose, methyl cellulose, hydroxypropylmethyl cellulose, carboxymethyl cellulose and the like; (2)vinylpolymers, such as polyvinyl alcohol, polyacrylic acid and its salt, polyvinyl pyrrolidone and the like; and (3)natural polymers, such as alginic acid, gum arabic, gum tragacanth, gelatine, starch, pullulan and the like. According to experiments carried out by the inventors, it has been revealed that among these water-soluble polymer material, Cellulose ethers remarkably improve the prolonged release effect of the prolonged release dosage form of the invention.

The prolonged release dosage form of the invention shows more preferable prolonged release properties than dosage forms prepared by only providing a coating layer on the surface of powder of medicinal agent, or by only mixing medicinal powder with an excipient and the like and tableting them.

Moreover, the granulation is carried out after forming a coating layer on the surface of the powder material of medicinal agent so that the problem of contraindication relating to combination of medicinal agent can be avoided and the fluidity of the medicinal particles improves. Thus, in preparing the prolonged release dosage form of the invention, the mixing operation at granulating is easily performed.

EXAMPLES

Now, the present invention will be described in detail with reference to examples.

EXAMPLE 1

Preparation of a Prolonged Release Dosage Form

Figure 3:
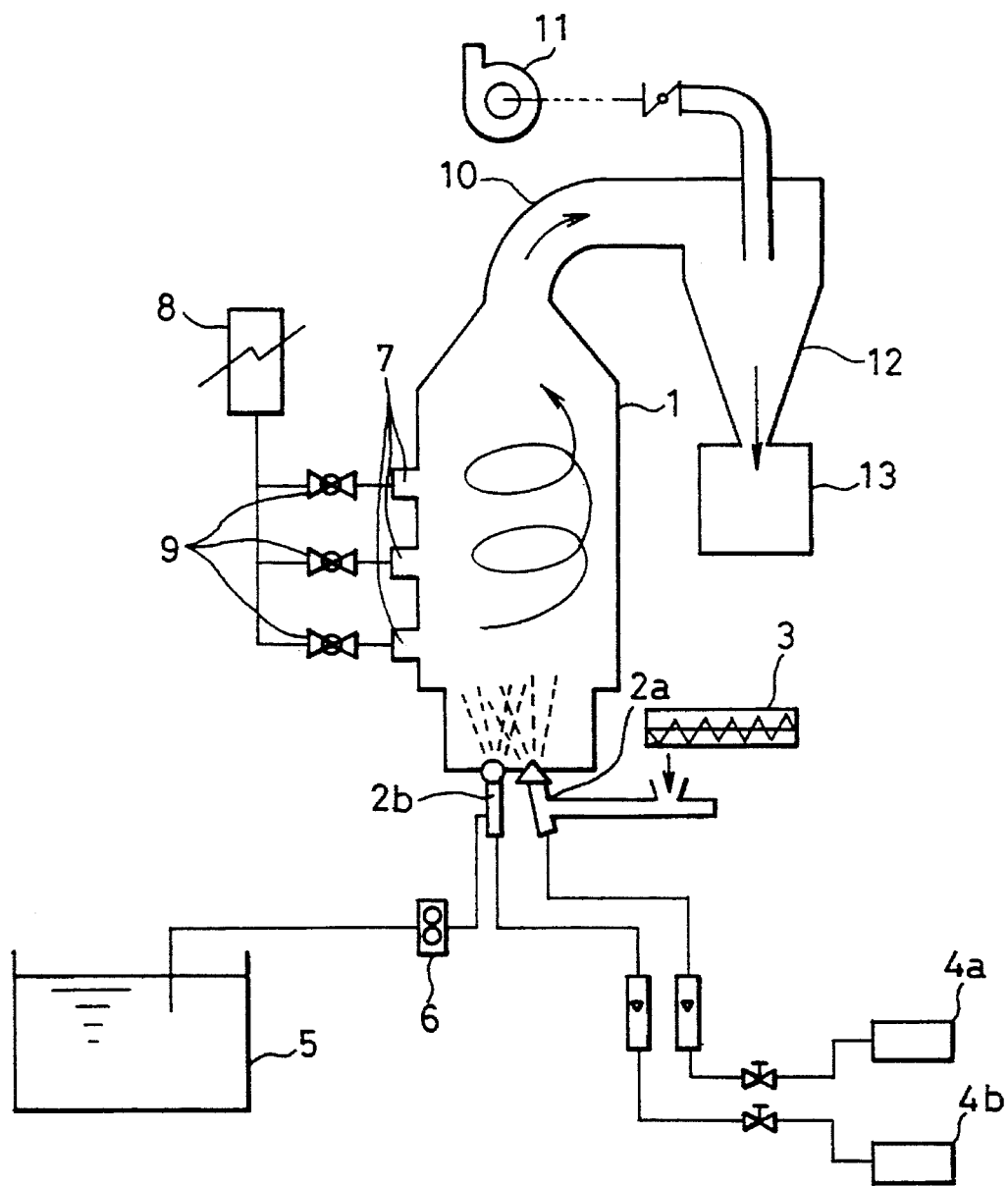
FIG. 3 is a schematic view showing a granulating-coating apparatus used for the invention.

For the formation of a coating layer, a granulating-coating apparatus shown in the aforementioned FIG. 3 ("Coatmizer", manufactured by Freund Industrial Co. Ltd.) was used. As ungranulated medicinal particles, powder material of theophylline (1–80 μm in longer diameter and 0.2–20 μm in shorter diameter) was used. As a water-insoluble material, a hydrogenated rape oil ("LW-102" produced by Freund Industrial Co. Ltd.) was used. The theophylline powder was jetted at a rate of 25 g/min., and the hydrogenated rape oil was dissolved in methylene chloride to prepare a 5% solution and jetted at a rate of 15 ml/min ("%" means "% by weight" throughout this specification). Drying air was blown at a temperature of 50° C. and at an amount of 5 $m^3$/min. The amount of coating with the hydrogenated rape oil was set to 15% of the theophylline.

Next, 5.5% of the obtained coated theophylline powder, 94% of a mixture of lactose and hydroxypropyl cellulose (8:2) as a vehicle, and 0.5% of magnesium stearate as a lubricant were, thus-obtained mixture was tableted to a dosage form of 8 mm in diameter, 190 mg in average weight and 4.5 kg in average hardness.

Dissolution Test

Figure 1:
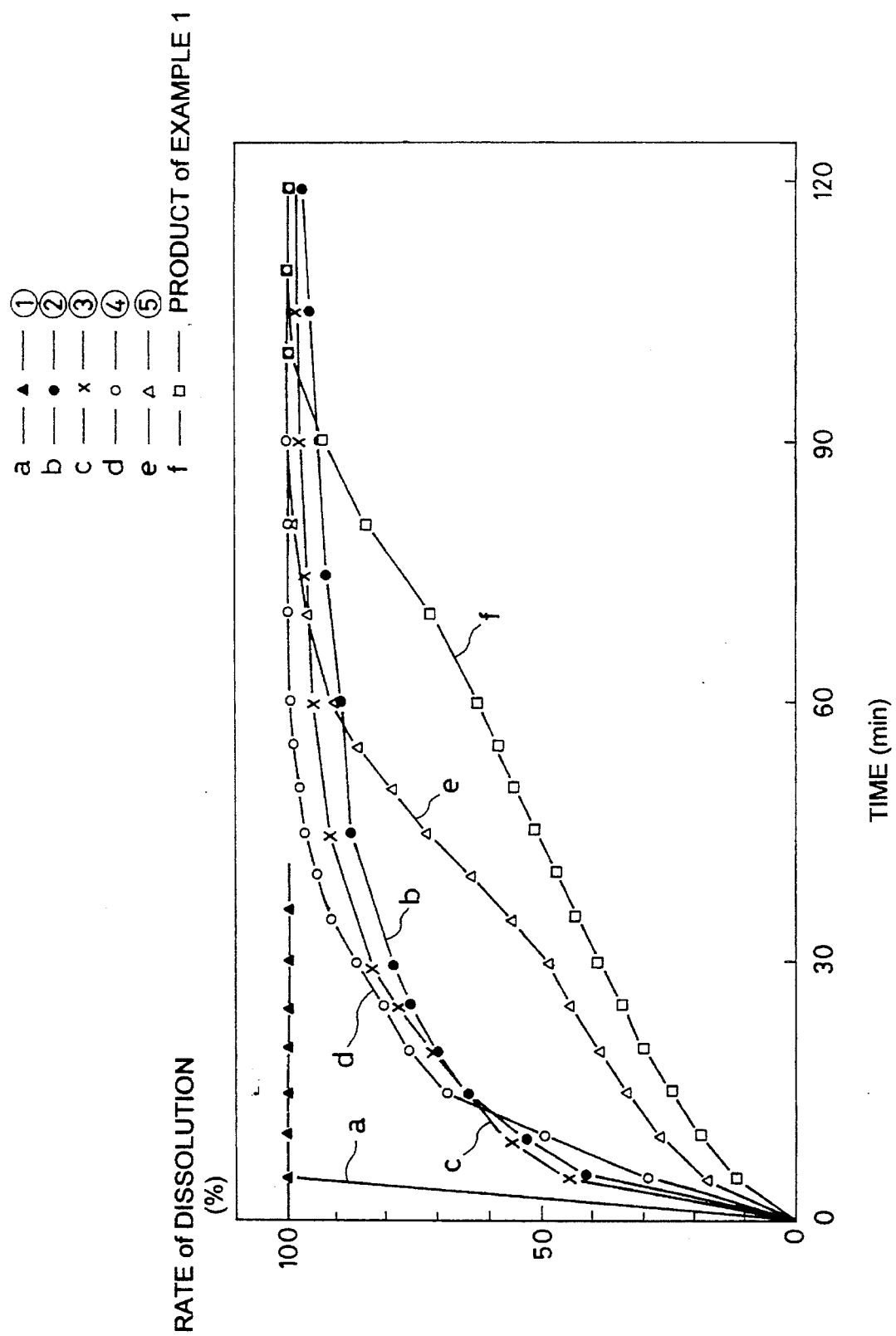
FIG. 1 is a graph showing the time courses of dissolved amounts in prolonged release dosage forms of the invention and comparative examples.

The time required for dissolution in water is shown in curve (f) of FIG. 1. Using an automatic dissolution test apparatus ("DT-600", manufactured by Japan Spectroscopic Co. Ltd.), the dissolved amount was measured by measuring absorption spectrum of the dissolved theophylline at a wavelength of 275 nm while mixing two tablets with 900 ml of purified water at a temperature of 37° C. by stirring with a paddle rotated at 100 rmp.

As comparative examples, dissolved amounts in powder and tablets obtained by various methods, ①–⑤ in water were measured by the same method as described above. For the cases of powder, the dissolution test was carried out using 20 mg of the powder.

① Theophylline Powder

The dissolution curve of the theophylline powder is shown by curve a in FIG. 1.

② Coated Theophylline Powder

The dissolution curve of the coated theophylline powder obtained in the present example (before tableting) is shown by curve b in FIG. 1.

③ Coated Theophylline Powder

In order to weaken the hydrophobic effect due to the wax (hydrogenated rape oil) on the coated theophylline powder obtained in the present example, a polyoxyethylene sorbitane monooleate-based surfactant ("Tween 80", produced by Kao Co. Ltd.) was added to the test liquid (purified water). The obtained dissolution curve is shown by curve c in FIG. 1.

④ Theophylline Powder Tablet

The powder of theophylline without any coating layer was mixed with an excipient and a lubricant, and the mixture was tableted. The excipient, the lubricant and the tableting conditions were the same as those described before. The dissolution curve of this tablet is shown by curve d in FIG. 1.

⑤ Tablet of Mixture of Theophylline Powder and Wax

Mixed powder of theophylline and fine-particled hydrogenated rape oil ("LW-103" produced by Freund Industrial Co. Ltd.) was prepared (85:15), an excipient and a lubricant were added, and the mixture was tableted. The excipient, the lubricant and the tableting conditions were the same as those described before. The dissolution curve of the obtained tablet is shown by curve e in FIG. 1.

Test Results

In the case of the powder of theophylline (①), the dissolution completed immediately (a). In the case of the tablet of the powder of theophylline (④), the dissolution curve (d) was of first order because of the dissolution suppressing effect of the hydroxypropyl cellulose used in the excipient. The wax-coated material powders (②, ③) showed almost the same dissolution curves (b,c), but they did not completely dissolve even after two hours. The one prepared by tableting after mixing with wax (⑤) showed a dissolution curve which is nearly a zero-ordered curve (a straight line) (e). However, the dissolution completed within about 70 minutes, therefore, apart from the shape of the dissolution curve, its prolonged release property was almost the same as those of ②, ③ and ④. In contrast to this, the dosage form of the present invention completed its dissolution within about 100 minutes and showed a dissolution curve with nearly a zero-order curve (a straight line), so that the prolonged release property was improved further. In general, particle size distribution is broad in a powder of medicinal agent, and therefore, it is expected that when a coating layer is formed on the surface thereof, the dissolution time differs from coated particle to coated particle and the dissolution curve becomes a broad one. But, unexpectedly, no such phenomenon was observed in the example. The reason for this may be attributed to the small particle size of the medicinal agent. Since it was small, the dispersion in dissolution time was negligibly small.

EXAMPLE 2

Figure 2:
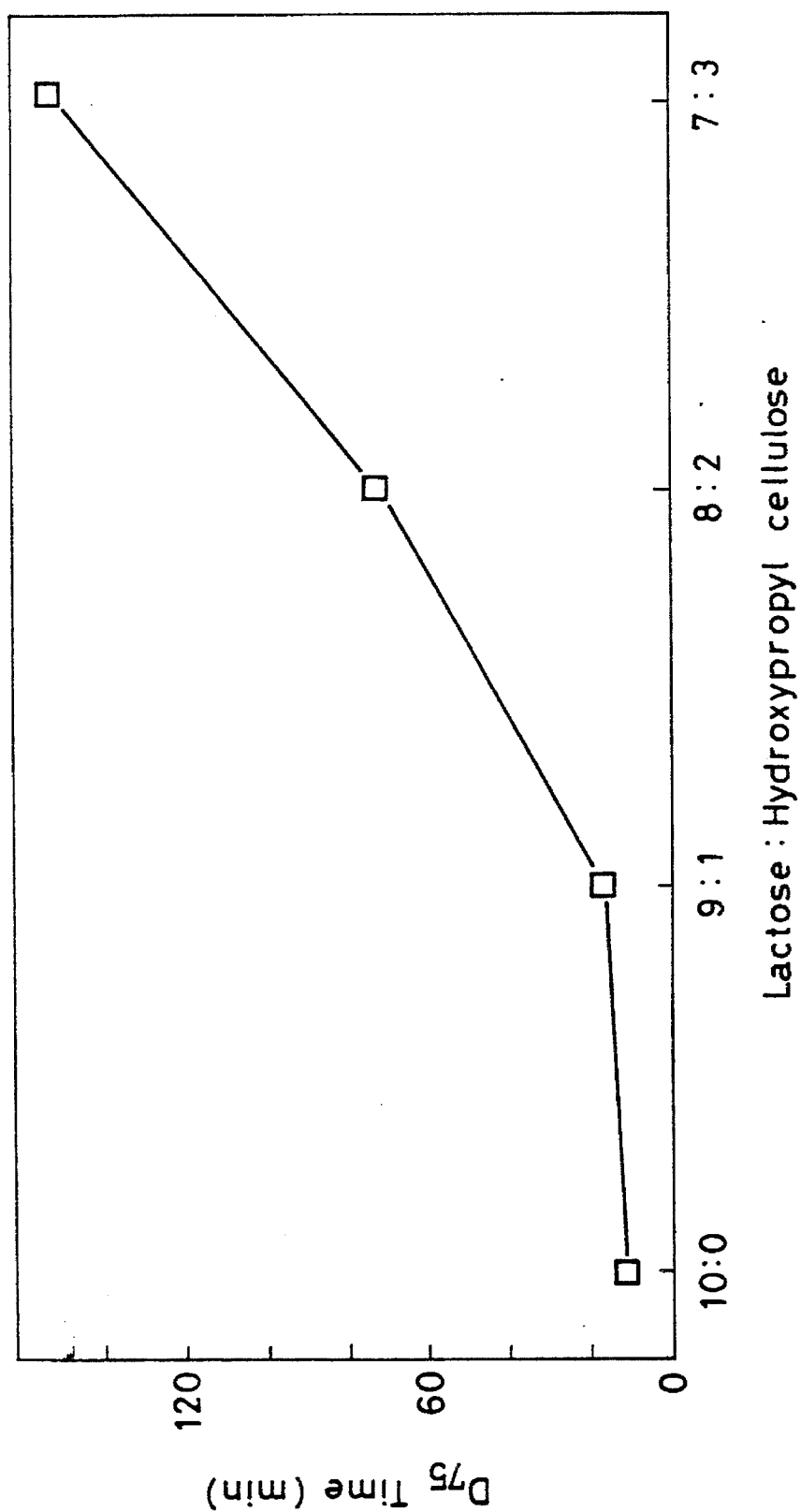
FIG. 2 is a graph showing the change in rate of dissolution of theophylline in a prolonged release dosage form of the invention prepared by varying the amount of addition of a water-soluble polymer material.

Prolonged release dosage forms were prepared and tested in the same method as in the aforementioned Example 1, except that the mixing ratio between lactose and hydroxypropyl cellulose in an excipient was changed. FIG. 2 shows the time in which the ratio of dissolution (D) of theophylline becomes 75%.

As can be seen in this Figure, the prolonged release property was further improved by adding hydroxypropyl cellulose in an excipient.

What is claimed is:

1. A method for producing a prolonged release form of drug, which comprises;

(1) obtaining a coated ungranulated medicinal particle by:
   jetting a solution or a liquid dispersion from a first nozzle and jetting an ungranulated medicinal particle from a second nozzle into a processing vessel from without said vessel without altering the size of said medicinal particle in said vessel, said solution or liquid dispersion containing a compound which is physiologically acceptable and does not dissolve in members selected from the group consisting of water and gastric juice, and said ungranulated medicinal particle having a size when jetted into said vessel within a range of from 0.1 to 100 μm, said jets colliding to adhere the solution or the liquid dispersion on the surface of the ungranulated medicinal particle to form a coating layer of the compound on the particle;
   drying the coated medicinal particle in the processing vessel; and subsequently,
   (2) granulating or tableting the coated and dried medicinal particles.

2. The method according to claim 1, wherein:

the compound is hydrophobic.

3. The method according to claim 1, wherein:

when granulating or tableting the coated medicinal particles, a water-soluble polymer is added to the coated medicinal particles, the water-soluble polymer being selected from the group consisting of synthetic cellulose ethers, vinyl-polymers and naturally occurring polymers selected from the group consisting of an alginic acid, gum arabic, gum tragacanth, gelatin, starch and pullulan.

4. The method of claim 1 wherein the compound is a water-insoluble polymer.

5. The method of claim 1 wherein the compound is a gastric juice insoluble polymer.

* * * * *